United States Patent [19]
Nagai et al.

[11] Patent Number: 5,164,416
[45] Date of Patent: Nov. 17, 1992

[54] TRANSDERMAL THERAPEUTIC FORMULATION CONTAINING A LIMONENE

[75] Inventors: Tsuneji Nagai, Tokyo; Kozo Takayama, Kawagoe; Hideaki Okabe, Urawa, all of Japan

[73] Assignee: Lintec Corporation, Tokyo, Japan

[21] Appl. No.: 700,046

[22] Filed: May 8, 1991

Related U.S. Application Data

[63] Continuation-in-part of Ser. No. 471,863, Jan. 29, 1990, abandoned.

[30] Foreign Application Priority Data

Feb. 3, 1989 [JP] Japan .................................... 1-26322

[51] Int. Cl.$^5$ .................. A61K 31/015; A61K 31/60; A61K 31/515
[52] U.S. Cl. .................... 514/763; 514/165; 514/270; 514/404; 514/420; 514/570; 514/663; 514/667; 514/686; 514/817; 514/947
[58] Field of Search ............... 514/763, 789, 947, 165, 514/270, 404, 420, 570, 663, 667, 686, 817

[56] References Cited

U.S. PATENT DOCUMENTS

| | | | |
|---|---|---|---|
| 3,023,144 | 2/1962 | Grethouse | 514/164 |
| 3,797,494 | 3/1974 | Zaffaroni | 424/434 |
| 4,254,145 | 3/1981 | Birnbaum | 514/530 |
| 4,336,151 | 6/1982 | Like et al. | 252/106 |
| 4,379,168 | 4/1983 | Dotolo | 514/763 |
| 4,474,798 | 10/1984 | Inagi et al. | 514/420 |
| 4,593,048 | 6/1986 | Sato et al. | 514/778 |
| 4,594,243 | 6/1986 | Satoh et al. | 424/78 |
| 4,710,497 | 12/1987 | Heller et al. | 514/221 |
| 4,912,125 | 3/1990 | Huebner et al. | 514/402 |

OTHER PUBLICATIONS

Merck Index, p. 788, 10th Edition, Entry No. 5321 "Limonene" (1983).

Primary Examiner—Richard L. Raymond
Assistant Examiner—Gary E. Hollinden
Attorney, Agent, or Firm—Frishauf, Holtz, Goodman & Woodward

[57] ABSTRACT

A transdermal therapeutic formulation comprising d-limonene and at least one pharmaceutically active substance wherein the content of the d-limonene is in the range from 0.1 to 2 weight percent, based on the total amount of the formulation. The transdermal therapeutic formulation has an excellent percutaneous absorption, is safe and is capable of delivering desired pharmaceutically active substances to a desired location of treatment or to the entire body of a patient through the circulatory system and is thus effective for curing various diseases.

14 Claims, 6 Drawing Sheets

TRANSDERMAL THERAPEUTIC FORMULATION CONTAINING A LIMONENE

CROSS-REFERENCE TO RELATED APPLICATION

This is a continuation-in-part application of application Ser. No. 07/471,863, filed Jan. 29, 1990 now abandoned.

BACKGROUND OF THE INVENTION

1. Field of the Invention

The present invention relates to a therapeutic formulation which is utilized with percutaneous absorption.

More particularly, the present invention relates to a transdermal therapeutic formulation which is excellent in both of percutaneous absorption and safety, capable of delivering desired pharmaceutically active substances rapidly to a desired location of treatment or to the whole parts of the body through the circulating system and thus effective for curing various kinds of disease.

2. Prior Art

During the recent progress of medical treatment, transdermal therapeutic systems(TTS) have been developed. In these systems, desired pharmaceutical substances are absorbed percutaneously and delivered to the whole parts of the body and thus the curing effect can be maintained for a prolonged time. For example, systems which are practiced recently utilize, as the pharmaceutically active substances, drugs for angina pectoris, such as nitroglycerin and isosorbide dinitrate, drugs for hypertonia, such as clonidine and drugs for climacteric difficulties, such as estradiol.

However, even though these transdermal therapeutic systems show many advantages such as evasion of metabolism of the pharmaceutically active substances at the intestine and liver, reduction of side reactions and increased maintenance of the pharmaceutical effect, they have defects that, because skin essentially has the barrier function against invasion of foreign substances, only limited kinds of pharmaceutically active substances can attain the concentration of the substances in blood high enough to show the pharmaceutical effect and the pharmaceutically active substances which can be utilized for the systems are naturally very limited.

Various methods have been tried so far to improve the percutaneous absorption of the pharmaceutically active substances. For example, pharmaceutically active substances were modified to form prodrugs and complexes and ionic pharmaceutically active substances were utilized in connection with ion tophoresis. These methods have a problem that the actual application requires detailed studies on the individual pharmaceutically active substance and a long period of time and a large amount of investment are inevitably required. On the other hand, development of percutaneous absorption promoters which increase percutaneous absorption of pharmaceutically active substances by decreasing the barrier property of skin has been actively made. It is expected that, by the use of these absorption promoters, various kinds of pharmaceutically active substances can be utilized without much limitation.

Examples of such percutaneous absorption promoters are polar solvents such as dimethyl sulfoxide, decyl methyl sulfoxide, dimethyl formamide, dimethyl acetamide and the like, cycloalkanes such as 1-dodecylazacycloheptan-2-one and the like, esters of alcohols and carboxylic acids such as isopropyl myristate, isopropyl palmitate and the like, surface active agents such as glycols, sodium lauryl sulfate and the like and derivatives of natural moisturizing factors of skin such as fatty acids, pyroglutamic acid, urea and the like. However, these absorption promoters cannot always satisfy both of the requirements on percutaneous absorption promotion and the requirements on safety. Furthermore, many of the promoters have a problem that the lag time of a drug absorption is considerably long and it takes a long time before the desired pharmaceutical effect is actually exhibited.

SUMMARY OF THE INVENTION

The present invention accordingly has an object to provide a transdermal therapeutic formulation which is excellent in both of percutaneous absorption and safety, capable of delivering desired pharmaceutically active substances rapidly to a desired location of treatment or to the whole parts of the body through the circulating system and thus effective for curing various kinds of disease.

Thus, the transdermal therapeutic formulation of the present invention comprises limonene and pharmaceutically active substances wherein the content of limonene is in the range from 0.1 to 30 weight percent based on the total amount of the formulation. More preferably, the limonene comprised in the formulation is d-limonene.

The present invention is particularly directed to a transdermal therapeutic formulation comprising d-limonene, at least one pharmaceutically active acidic substance, ethanol, water and a basic substance, wherein the pH of the formulation is from 5.5 to 7.5 and the content of the d-limonene is from 0.1 to 5 weight percent, preferably 0.1 to 2 weight percent and most preferably 1 to 2 weight percent, based on the total amount of the formulation.

DETAILED DESCRIPTION OF THE PREFERRED EMBODIMENTS

The inventors made intensive investigations to develop the transdermal therapeutic formulation having the above excellent characteristics to achieve the above mentioned object and, paying particular attention to the fact that limonene which is easily available in the nature has a function to remarkably promote the percutaneous absorption of pharmaceutically active substances and has excellent safety at the same time, discovered that the above mentioned object can be achieved by utilizing limonene as a component of the transdermal therapeutic formulation in a specified range of content.

The present invention provides a transdermal therapeutic formulation comprising a limonene and pharmaceutically active substances wherein the content of the limonene is in the range from 0.1 to 30 weight percent based on the total amount of the formulation.

The present invention will be explained in detail in the following.

Limonene which is utilized as the percutaneous absorption promoter in the invention comprises a dextro-rotatory compound and a levo-ratotory compound. The dextro-rotatory compound (d-limonene) is the main component of essential oil which is obtained from skin of citrus fruits, such as orange and lemon. On the other hand, the levo-rotatory compound (l-limonene) is contained in beefsteak plant oil and chenopodium oil. The racemic compound (d,l-limonene) is contained in Japanese pepper oil. A clear difference is not observed between these limonene compounds regarding the effect of percutaneous absorption promotion and any of these compounds can be utilized to promote percutaneous absorption of drugs in the invention. However, these limonene compounds smell differently from each other. Smell is another factor of evaluation concerning additives to drugs and, naturally, a bad smell is not preferred. From this point of view, d-limonene which smells like orange and lemon is particularly preferable.

It is essential that the content of the limonene in the transdermal therapeutic formulation of the invention is in the range from 0.1 to 30 weight percent based on the total amount of the formulation. When the content of the limonene is lower than 0.1 weight percent, the effect of the promotion of percutaneous absorption is not sufficient. When the content of the limonene is higher than 30 weight percent, the effect of the promotion of percutaneous absorption is not increased to a degree expected from the increase of the amount and, moreover, irritation of skin increases remarkably. The preferable content of the limonene is in the range from 1 to 5 weight percent from the point of view of the effect of percutaneous absorption promotion and the degree of skin irritation. However, the degree of skin irritation is different depending upon the kind of base materials and solvents utilized and the most preferable content of the limonene should be selected depending upon these conditions.

Because the limonene is highly lipophilic and hydrophobic, it is preferable that pharmaceutically allowable organic solvents, solubilizing agents, such as pyrrolidone, or surface active agents are utilized together with other ingredients. It is also a good practice that a suspension is prepared by using emulsifiers or dispersants.

A pharmaceutically active acidic substance for use in the present invention includes substances having a carboxylic acid group and substances without a carboxylic acid group.

Examples of pharmaceutically active acidic substances having a carboxylic acid group are indomethacin, ketoprofen, ibuprofen, flurprofen, fenoprofen, diclofenac, ibufenac, mefenac, mefenamic acid, flufenamic acid, salicylic acid and acetylsalicylic acid.

Examples of pharmaceutically active acidic substances without a carboxylic acid group are phenylbutazone, ketophenylbutazone, oxyphenbutazone, phenobarbital, amobarbital and cyclobarbital.

The preferred pharmaceutically active substances are indomethacin and ketoprofen.

The most preferred pharmaceutical active substance is indomethacin.

A basic substance for use in the present invention includes organic basic substances and inorganic basic substances.

Examples of an organic basic substance are an alkylamine, such as methylamine, ethylamine and propylamine; a dialkylamine, such as dimethylamine, diethylamine and dipropylamine; a trialkylamine, such as trimethylamine, triethylamine and tripropylamine; an alkanolamine, such as methanolamine, ethanolamine and propanolamine; a dialkanolamine, such as dimethanolamine, diethanolamine and dipropanolamine; and a trialkanolamine, such as trimethanolamine, triethanolamine and tripropanolamine.

Examples of an inorganic basic substance are sodium hydroxide and potassium hydroxide.

The preferred basic substance is triethanolamine.

The pH of the formulation of the invention is in the range from 5.5 to 7.5, preferably from 6 to 7.

The transdermal therapeutic formulation of the invention may be utilized, if desired, in combination with various kinds of pharmaceutically allowable additives, such as stabilizers, antiaging agents, antioxidants, perfumes, fillers and other kinds of percutaneous absorption promoters so long as the additives do not harm the object of the invention.

The method of utilization of the formulation of the invention is not particularly limited and any form of conventionally utilized external preparations, such as ointments, creams, gels, lotions, liquids, sprays, cataplasmas, tapes and the like, can be used.

As the base of ointments and creams, fatty oils, lanolin, vaseline, paraffins, plastibases, glycols, higher fatty acids, higher alcohols and the like are utilized. If necessary, stabilizers, preservatives, emulsifiers, dispersants and the like may be added to the base according to the needs. As the base of lotions, ethanol, glycerol, glycols and the like are utilized. As the base of liquids, ethanol, purified water, glycols and the like are utilized.

Examples of the base of cataplasmas are natural polymers, such as gelatin, sodium alginate, corn starch, traganth gum, casein and the like; celluloses, such as methyl cellulose, ethyl cellulose, hydroxyethyl cellulose, carboxymethyl cellulose and the like; starches, such as dextran, carboxymethyl starch and the like, and synthetic polymers, such as polyvinyl alcohol, sodium polyacrylate, polyvinyl pyrrolidone, polyvinyl ether and the like. If necessary, moisturizing agents, such as glycerol, propylene glycol and the like, inorganic fillers, such as kaolin, bentonite, zinc oxide and the like, thickness adjusting agents, pH adjusting agents, antioxidants and the like may be compounded to the base according to the needs.

As the adhesive for tapes and patches, for example, acrylic adhesives, rubber adhesives, silicone adhesives and the like are utilized. The adhesives can be made into microreservoir-type materials by dispersing the pharmaceutically active substance or a mixture of the pharmaceutically active substances and water soluble polymers within the adhesives. Dispersion of adhesives containing the pharmaceutically active substances within the base of cataplasma can also be utilized.

The acrylic adhesives comprise, as the main component thereof, at least one polymer selected from the group consisting of, for example, a homopolymer of acrylic ester, a copolymer comprising two or more kinds of acrylic ester unit and a copolymer of acrylic ester and other functional monomers. Examples of the acrylic ester are butyl (meth)acrylate, pentyl (meth)a- crylate, hexyl (meth)acrylate, heptyl (meth)acrylate, octyl (meth)acrylate, nonyl (meth)acrylate, decyl (meth)acrylate and the like. Examples of the functional monomer are monomers containing a hydroxyl group, such as hydroxyethyl (meth)acrylate, hydroxypropyl (meth)acrylate and the like, and monomers containing an amide group, such as (meth)acrylamide, dimethyl(meth)acrylamide and the like.

The acrylic adhesives can generally be divided into solvent-type adhesives and emulsion-type adhesives. The solvent-type adhesives generally comprise an acrylic polymer, solvents, crosslinking agents, adhesion promoters if desired and other ingredients. As the crosslinking system, methylol group crosslinking system, ionic crosslinking system, urethane crosslinking system, epoxy crosslinking system and the like are utilized. The emulsion-type adhesives generally comprise an acrylic polymer, emulsifiers, aqueous solvents, adhesion promoters if desired and other ingredients.

The rubber adhesives comprise, as the main component thereof, at least one polymer selected from the group consisting of, for example, natural rubber, polyisoprene rubber, polyisobutylene rubber, polybutadiene rubber, styrene-butadiene-styrene block copolymer and styrene-isoprene-styrene block copolymer. Adhesion promoters, plasticizers, antioxidants, fillers and the like may be compounded with the rubber adhesives, if desired. The solvent-type adhesives and the emulsion-type adhesives using rubber latexes are preferably utilized.

The silicone adhesives comprise, as the main component thereof, polydimethylsiloxane, polydiphenylsiloxane and the like. The solvent-type adhesives comprising adhesion promoters, plastisizers, filler and the like are preferably utilized.

The adhesion promoters compounded with the adhesives according to the desire are, for example, natural resins, such as rosin resins, polyterpene resins and the like, petroleum resins such as C5 resins, C9 resins, DCPD resins and the like and synthetic resins, such as cumarone-indene resins, xylene resins and the like.

The base utilized for the tapes are, for example, sheets and films of synthetic resins, such as polyester, polyvinyl chloride, polypropylene, polyethylene, polyurethane and the like, synthetic papers, sheets and films of cellulose, non-woven cloths, woven cloths, knitted cloths and the like.

The effect which is exhibited by the drug of the invention can be explained by the following mechanism. It is the general understanding that the barrier property of skin against foreign substances is based upon the structure of stratum corneum. This is more easily understood when one observes remarkably increased penetration of pharmaceutically active substances through skin when the surface of the skin is partially removed by some cause, for example by cleavage of tape attached to the skin. The stratum corneum of skin is composed of layers of keratin cells which are made of proteins of flattened structures. There are two routes of passage for pharmaceutically active substances: the transcellular route which is the passage through cells and the intercellular route which is the passage through interstices between cells. The stratum corneum cells are composed of keratin and lipids and, at the intercellular route, lamella layers are formed by amphiphilic materials such as phospholipids and the like, thus hydrophilic layers and lipophilic layers are accumulated to form a multilayer area. In the hydrophilic layers, molecules of water aggregate together to form clusters. Both of the hydorphilic and lipophilic layers show high resistance against diffusion of foreign substances and the general understanding is that the barrier property of skin is caused by the tight structure of the skin layers as described here.

Limonene is considered to have a particularly high affinity to lipids, is capable of loosening the lipid structure, increases the fluidity of the lipids, decreases the resistance to diffusion and thus enhances the permeability of pharmaceutically active substances. It also affects the structure of water molecules in the hydrophilic layer to a considerable degree through actions on lipids, thus causing the increase of the permeability of the active substances.

In the following, examples are given to illustrate the drug of the invention in more detail, but not to limit the scope of the invention in any sense.

EXAMPLE 1 AND EXAMPLE 2; COMPARATIVE EXAMPLES 1 THROUGH 3

By using male rats of the Wistar strain having a weight of 160 to 190 g, percutaneous absorption of a pharmaceutically active substance, indomethacin, was examined.

Hairs of the abdominal area of a rat were removed by using an animal clipper and a glass cell of a cylinder shape having an inner diameter of 16 mm and a height of 10 mm was fixed at the area by using an adhesive.

Figure 1:
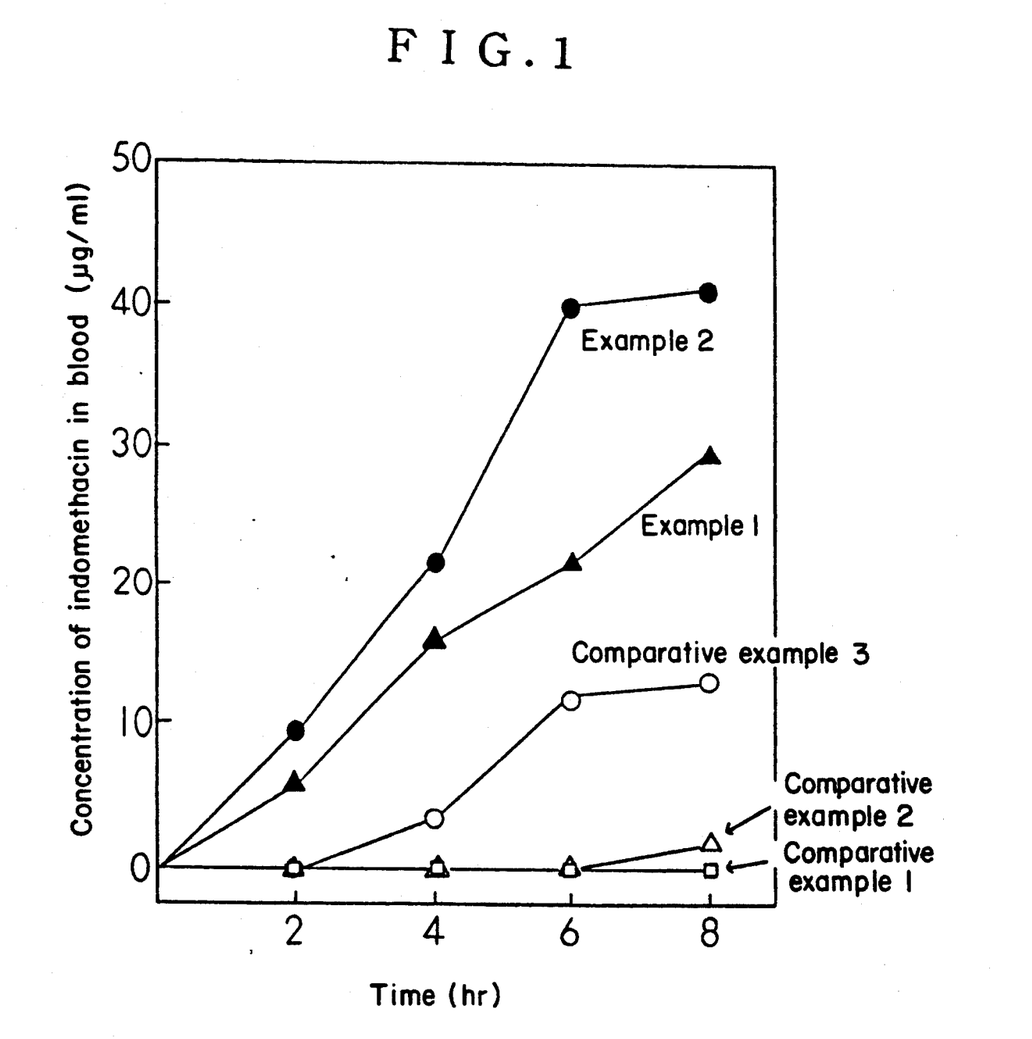
FIG. 1, FIG. 2 and FIG. 3 show the relationships between the length of time during which the drugs were applied and the concentration of the pharmaceutically active substances in blood when gel ointments of various compositions were applied to rats abdominal skin.

Gel ointments having the compositions shown in Table 1 were prepared and 1 g of each gel ointment was applied for evaluation. After the application of the ointment, a sample of blood was taken from time to time via the juglar vein and the concentration of indomethacin in the blood was measured by using the high performance liquid chromatography. The relationships between the concentration of indomethacin in blood and time after the application are shown in FIG. 1.

TABLE 1

| | | Example | | Comparative example | | |
|---|---|---|---|---|---|---|
| | | 1 | 2 | 1 | 2 | 3 |
| Composition of gel ointment (weight percent) | Indomethacin | 1.0 | 1.0 | 1.0 | 1.0 | 1.0 |
| | Carboxyvinyl polymer | 2.0 | 2.0 | 2.0 | 2.0 | 2.0 |
| | Triethanolamine | 2.5 | 2.5 | 2.5 | 2.5 | 2.5 |
| | Ethanol | 50.0 | 50.0 | 50.0 | 50.0 | 50.0 |
| | Water | 43.5 | 42.5 | 44.5 | 43.5 | 42.5 |
| | d-Limonene | 1.0 | 2.0 | — | — | — |
| | Azone ® 1) | — | — | — | 1.0 | 2.0 |

1) Azone ®: 1-dodecylazacycloheptan-2-one

The pH of the composition of Example 1 is 6.6 and the pH of the composition of Example 2 is 6.5.

EXAMPLE 3 AND COMPARATIVE EXAMPLE 4

Using ketoprofen as the pharmaceutically active substance, a gel ointment having the composition shown in Table 2 was prepared and the percutaneous absorption was examined in the same way as described in the previous examples. The relationship between the concentration of ketoprofen in the blood and time after the application is shown in FIG. 2.

EXAMPLE 4 AND COMPARATIVE EXAMPLE 5

Using sodium diclofenac as the pharmaceutically active substance, a gel ointment having the composition shown in Table 3 was prepared and the percutaneous absorption was examined in the same way as described in the previous examples. The relationship between the concentration of sodium diclofenac in the blood and time after the application is shown in FIG. 3.

Figure 2:
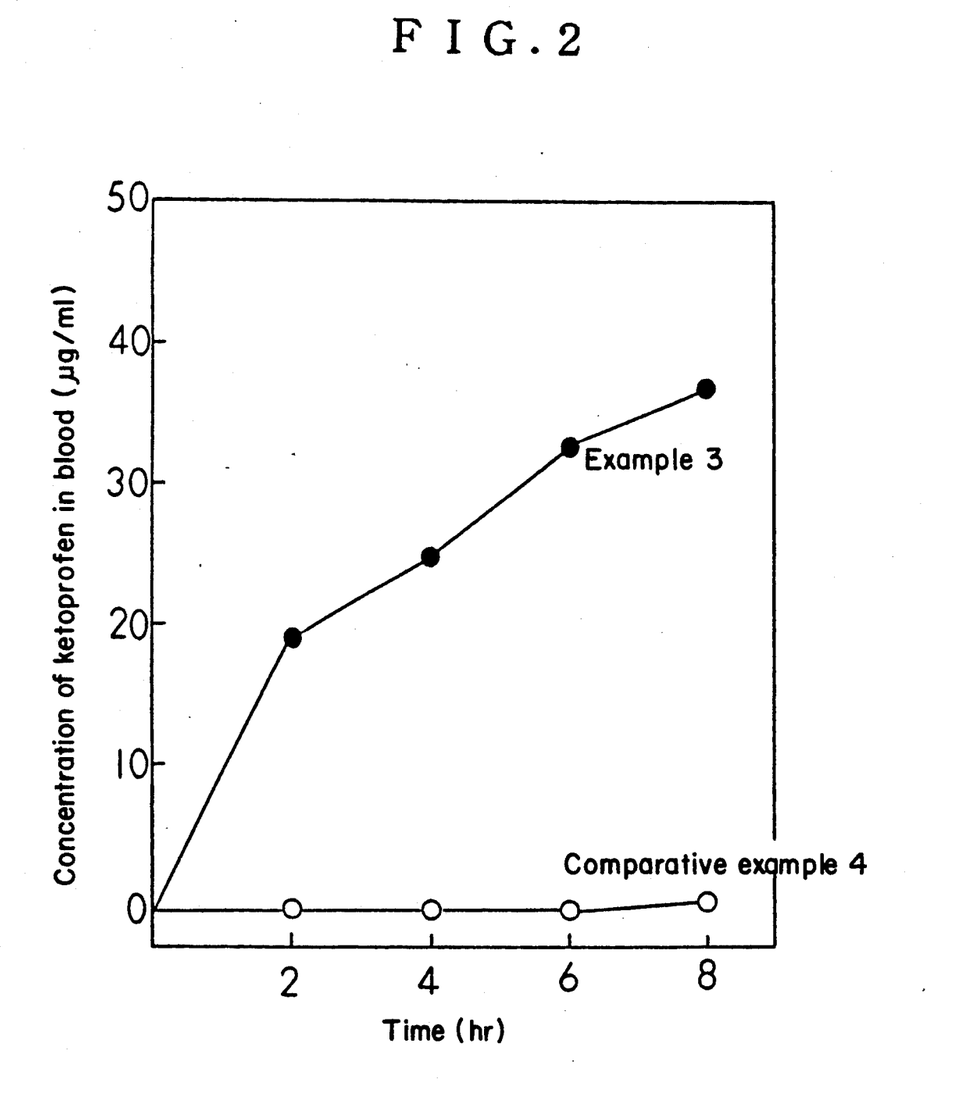
Figure 3:
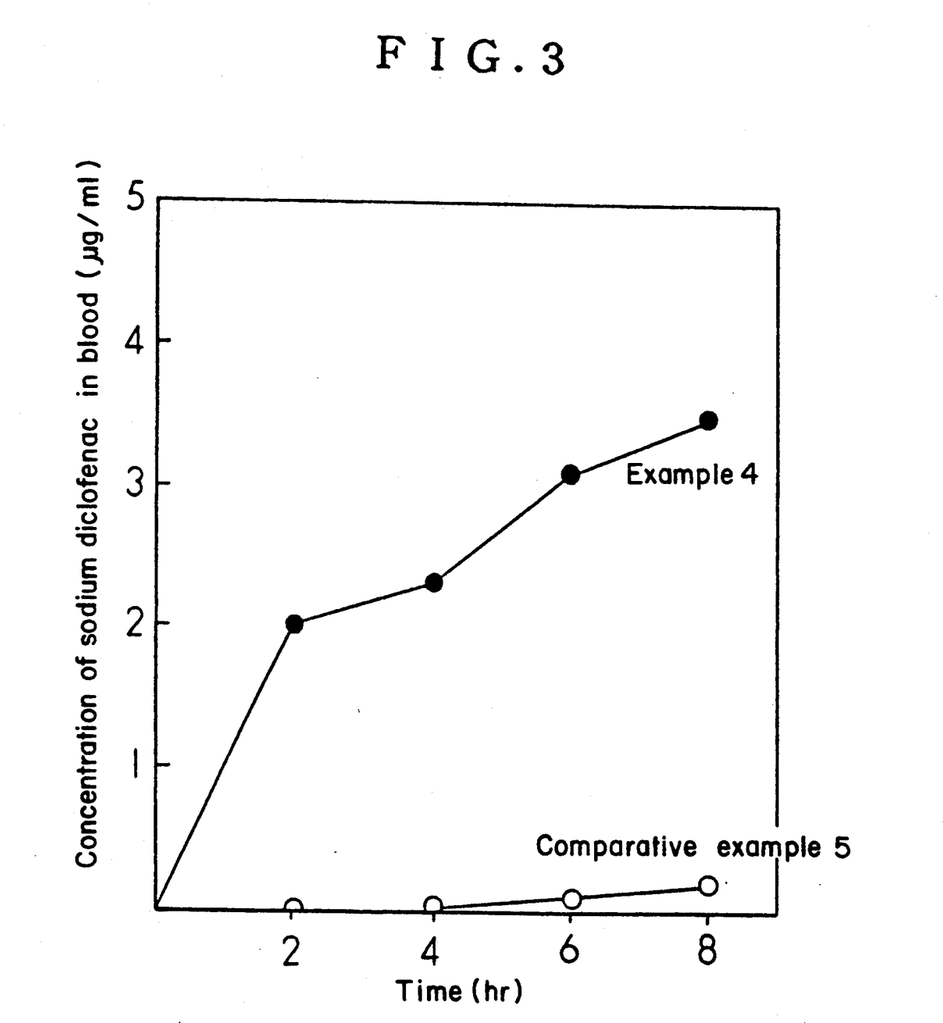

As shown in FIG. 1 through FIG. 3, the gel ointments of the invention which comprise d-limonene are all excellent in the percutaneous absorption of the pharmaceutically active substances when they are compared with those without the limonene. The ointment of Comparative example 3 in which 2 weight percent of azone was compounded showed a small degree of improvement in the percutaneous absorption, but the degree of improvement was much smaller than the improvement shown by the ointment in which 2 weight percent of d-limonene was compounded.

TABLE 2

|  |  | Example 3 | Comparative example 4 |
|---|---|---|---|
| Composition of gel ointment (weight percent) | Ketoprofen | 3.0 | 3.0 |
|  | Carboxyvinyl polymer | 2.0 | 2.0 |
|  | Triethanolamine | 2.5 | 2.5 |
|  | Ethanol | 50.0 | 50.0 |
|  | Water | 40.5 | 42.5 |
|  | d-Limonene | 2.0 | — |

The pH of the composition of Example 3 is 6.2.

TABLE 3

|  |  | Example 4 | Comparative example 5 |
|---|---|---|---|
| Composition of gel ointment (weight percent) | Sodium diclofenac | 3.0 | 3.0 |
|  | Carboxyvinyl polymer | 2.0 | 2.0 |
|  | Triethanolamine | 2.5 | 2.5 |
|  | Ethanol | 40.0 | 40.0 |
|  | Water | 51.5 | 53.5 |
|  | d-Limonene | 2.0 | — |

The pH of the composition of Example 4 is 6.9.

EXAMPLE 5

The examination of the percutaneous absorption of indomethacin was made in the same way as that in Example 1 except that l-limonene was used in place of d-limonene and the same degree of the effect on the percutaneous absorption promotion as that of d-limonene was observed.

The pH of the composition of Example 5 is 6.5.

While d-limonene has a pleasant smell resembling lemon and orange, l-limonene has a slightly unpleasant smell.

COMPLEMENTARY EXAMPLE 1

Ethanol solutions of d-limonene and Azone ® (1-dodecylazacyclo-heptan-2-one) with varying concentrations were prepared and served as the samples of the examination.

Figure 4:
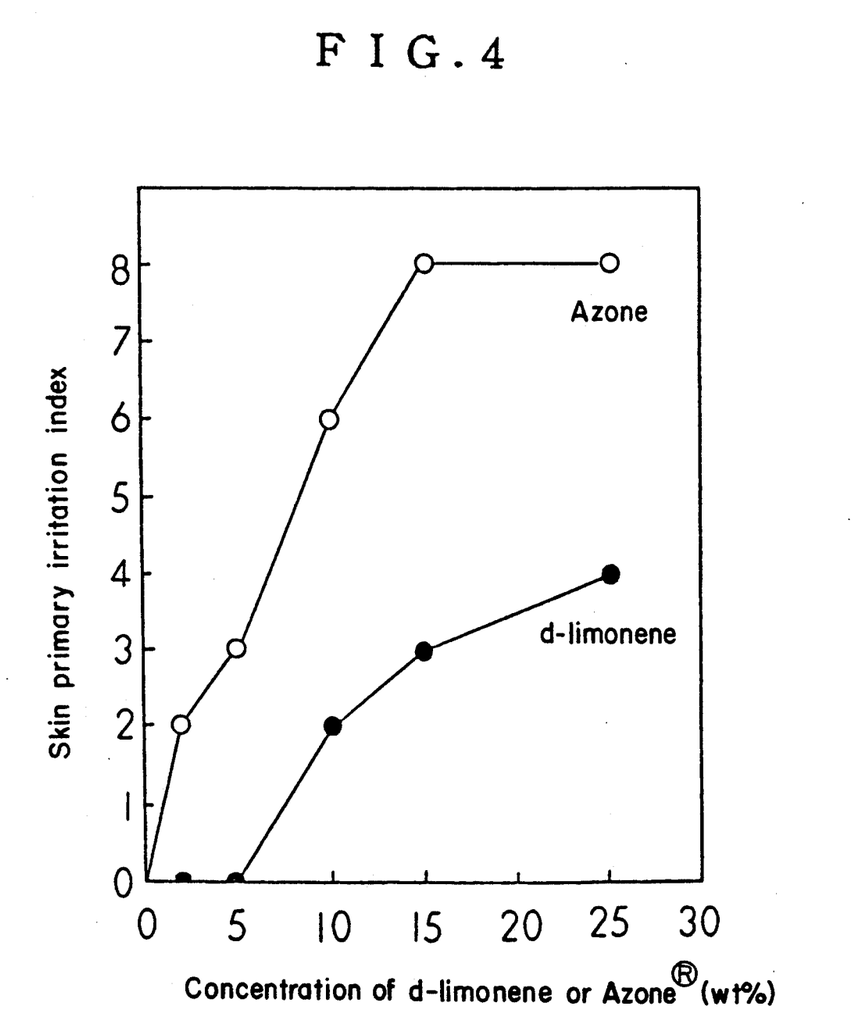
FIG. 4 shows the relationship between the concentration of d-limonene or Azone ® in ethanol solution and the skin primary irritation index.
Figure 5:
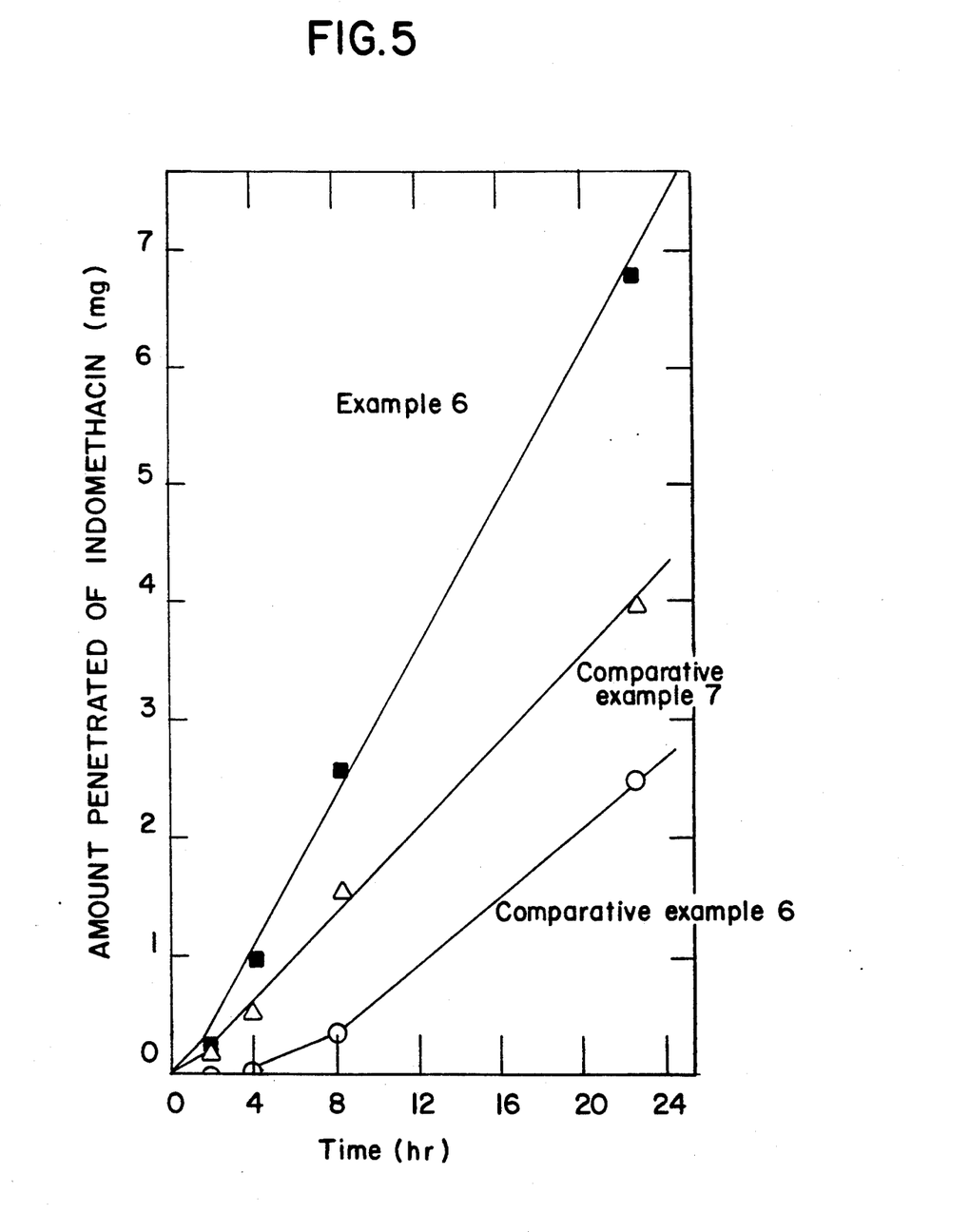
FIG. 5 is a graph of the amount penetrated of indomethacin (mg) vs. time (hours) for Comparative Examples 6 and 7.
Figure 6:
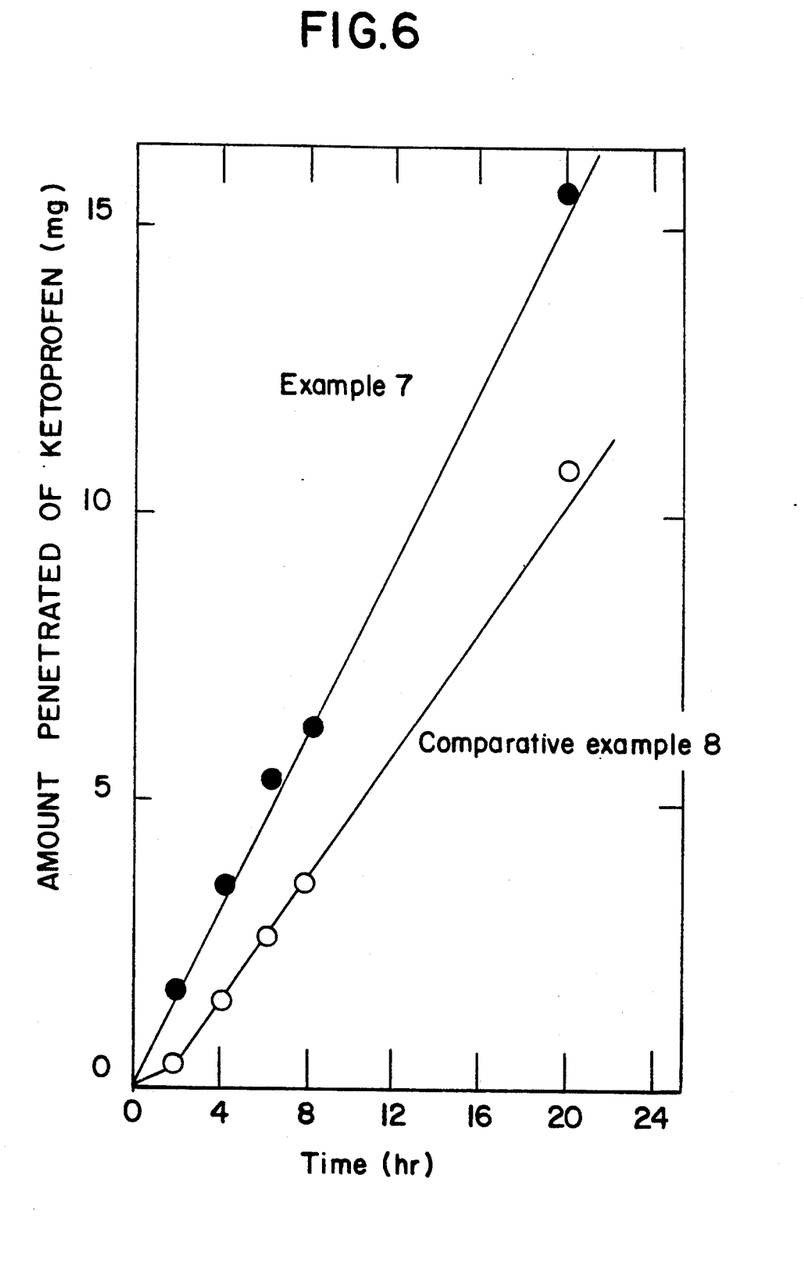
FIG. 6 is a graph of the amount penetrated of ketoprofen (mg) vs. time (hours).

Hairs of back of the a white rabbit having a weight of about 1.5 kg were removed by using an animal clipper and, after keeping the rabbit for 24 hours, adhesive plasters for patch testing containing the above described samples were applied to the skin. The patch testing was made according to the Draize method and the primary irritation indices on skin were obtained. FIG. 4 shows the relationship between the concentration of d-limonene or Azone ® and the index.

It is clearly understood from FIG. 4 that d-limonene has a much less degree of irritation on skin than Azone ®, that d-limonene has very little effect of irritation to skin when the concentration of d-limonene is lower than 5 percent and that, because d-limonene has a remarkable promoting effect on the percutaneous absorption even when the concentration is only 1 to 2 weight percent, d-limonene can be evaluated to be useful for practical purposes as the promoting agent of percutaneous absorption of pharmaceutically active agents.

COMPLEMENTARY EXAMPLE 2

Compounds shown in Table 4 including limonenes and conventionally known percutaneous absorption promoters were examined regarding their smell by the method of organoleptic testing by a group of 5 persons. Evaluation was made according to the following classification:

| o: point 1 | no smell or pleasant |
|---|---|
| Δ: point 2 | weak smell or agreeable |
| x: point 3 | a little unpleasant |
| xx: point 4 | disagreeable |

The evaluation was made by each panel member by classifying the smell of each compound into one of the four classes shown above and the values obtained were averaged and rounded to give the final results which are shown in Table 4.

TABLE 4

| Compound examined | Evaluation of smell |
|---|---|
| l-Nonene | xx |
| p-Menthane | x |
| α-Terpinene | Δ |
| n-Butylcyclohexane | Δ |
| t-Butylcyclohexane | Δ |
| Ethylcyclohexane | Δ |
| Biphenyl | x |
| n-Butylbenzene | x |
| Myrcene | xx |
| Dicyclohexyl | o |
| Dimethylnaphthalene | x |
| p-Cymene | x |
| Dicyclopentadiene | x |
| 1,5-Cyclopentadiene | xx |
| Cyclooctane | x |
| Isooctane | Δ |
| l-Dodecene | xx |
| d-Limonene | o |
| l-Limonene | x |
| dl-Limonene (Dipentene) | Δ |

Dicyclohexyl has a smell as good as d-limonene but is inferior to d-limonene, concerning the promoting effect of percutaneous absorption.

Examples 6 and 7 and Comparative Examples 6, 7 and 8

Skin of rats of the Wistar strain was set in a Frantz type glass cell. Each composition shown in Table 5 was applied to a donor side of the cell and a buffer solution containing phosphoric acid having a pH of about 7.2 was applied to a receiver side of the cell. The amount penetrated of the pharmaceutically active acidic substance was measured by using high performance liquid chromatography.

TABLE 5

|  |  | Example | | Comparative example | | |
|---|---|---|---|---|---|---|
|  |  | 6 | 7 | 6 | 7 | 8 |
| Composition (g) | d-limonene | 2 | — | 0 | 2 | 2 |
|  | Indomethacin | 1 | — | 1 | 1 | — |

TABLE 5-continued

|  | Example | | Comparative example | | |
|---|---|---|---|---|---|
|  | 6 | 7 | 6 | 7 | 8 |
| Ketoprofen | — | 2 | — | — | 2 |
| Ethanol | 70 | 70 | 70 | 70 | 70 |
| Water | 30 | 30 | 30 | 30 | 30 |
| Triethanolamine | 0.3 | 0.7 | — | — | — |
| pH value | 6.5 | 6.4 | 4.2 | 4.2 | 4.3 |

To summarize the advantages obtained by the invention, the transdermal therapeutic formulation comprises, as the percutaneous absorption promoter, a limonene which is excellent in both of percutaneous absorption and safety and is capable of delivering desired pharmaceutically active substances rapidly to a desired location of treatment or to the whole parts of the body through the circulating system and thus is effective for curing various kinds of disease.

What is claimed is:

1. A transdermal therapeutic formulation comprising d-limonene, at least one pharmaceutically active acidic substance, ethanol, water and a basic substance, wherein the pH of the formulation is from 5.5 to 7.5 and the content of the d-limonene is from 0.1 to 2 weight percent based on the total amount of the formulation.

2. The transdermal therapeutic formulation of claim 1, wherein the pharmaceutically active acidic substance is selected from the group consisting of indomethacin, ketoprofen, ibuprofen, flurprofen, fenoprofen, diclofenac, ibufenac, mefenac, ibufenac, mefenamic acid, flufenamic acid, salicylic acid, acetylsalicylic acid, phenylbutazone, ketophenylbutazone, oxyphenbutazone, phenobarbital, amobarbital and cyclobarbital.

3. The transdermal therapeutic formulation of claim 2, wherein the basic substance is selected from the group consisting of an alkylamine, a dialkylamine, a trialkylamine, an alkanolamine, a dialkanolamine, a trialkanolamine and an inorganic basic substance.

4. The transdermal therapeutic formulation according to claim 2, wherein the basic substance is selected from the group consisting of methylamine, ethylamine, propylamine, dimethylamine, diethylamine, dipropylamine, trimethylamine, triethylamine, tripropylamine, methanolamine, ethanolamine, propanolamine, dimethanolamine, diethanolamine, dipropanolamine, trimethanolamine, triethanolamine, tripropanolamine, sodium hydroxide and potassium hydroxide.

5. The transdermal therapeutic formulation of claim 1, wherein the basic substance is triethanolamine.

6. The transdermal therapeutic formulation of claim 1, wherein the pH of the formulation is 6 to 7.

7. The transdermal therapeutic formulation of claim 1, wherein the active substance is selected from the group consisting of indomethacin and ketoprofen; the basic substance is triethanolamine; and the pH of the formulation is 6 to 7.

8. The transdermal therapeutic formulation of claim 1, wherein the content of the d-limonene is 1 to 2 weight percent.

9. The transdermal therapeutic formulation claim 1, wherein the pharmaceutically active substance is indomethacin.

10. The transdermal therapeutic formulation in claim 1, wherein the pharmaceutically active substance is sodium diclofenac.

11. The transdermal therapeutic formulation of claim 1, wherein the pharmaceutically active substance is ketoprofen.

12. A method for percutaneously administering at least one pharmaceutically active acidic substance to a patient comprising topically applying the pharmaceutically active acidic substance in a formulation with d-limonene, ethanol, water and a basic substance, wherein the content of d-limonene is 0.1 to 2 weight percent, based on the total weight of the formulation and wherein the pH of the formulation is 5.5 to 7.5.

13. The method of claim 12, wherein the content of the d-limonene is 1 to 2 weight percent.

14. The method of claim 12, wherein the active substance is selected from the group consisting of indomethacin, sodium diclofenac and ketoprofen.

* * * * *